US 6,745,628 B2

(12) United States Patent
Wunderer

(10) Patent No.: US 6,745,628 B2
(45) Date of Patent: Jun. 8, 2004

(54) METHOD AND APPARATUS FOR TESTING THIN MATERIAL

(75) Inventor: Bernd Wunderer, München (DE)

(73) Assignee: Giesecke & Devrient GmbH, Munich (DE)

( * ) Notice: Subject to any disclaimer, the term of this patent is extended or adjusted under 35 U.S.C. 154(b) by 4 days.

(21) Appl. No.: 10/206,234

(22) Filed: Jul. 29, 2002

(65) Prior Publication Data

US 2003/0025512 A1 Feb. 6, 2003

(30) Foreign Application Priority Data

Jul. 31, 2001 (DE) .......................................... 101 37 389

(51) Int. Cl.⁷ .............................................. G01N 29/00
(52) U.S. Cl. ............................. 73/579; 73/599; 73/627; 73/159
(58) Field of Search .......................... 73/579, 598, 599, 73/600, 596, 573, 627, 644, 602, 159, 618, 619, 620, 624, 616, 625, 628, 633, 641

(56) References Cited

U.S. PATENT DOCUMENTS

| 4,442,715 A | | 4/1984 | Brisken et al. |
| 4,519,249 A | | 5/1985 | Hunt |
| 5,361,767 A | * | 11/1994 | Yukov ........................ 600/442 |
| 5,591,913 A | | 1/1997 | Tucker |
| 5,932,806 A | | 8/1999 | Rose et al. |
| 5,947,902 A | * | 9/1999 | Goll et al. .................. 600/442 |
| 6,468,215 B1 | * | 10/2002 | Sarvazyan et al. .......... 600/438 |
| 6,595,060 B2 | * | 7/2003 | Wunderer et al. ............ 73/597 |

FOREIGN PATENT DOCUMENTS

DE 198 52 715 6/1999

OTHER PUBLICATIONS

WPIDS Abstract: 1991–206094/28 zu SU 1587347 A.
WPIDS Abstract: 1982–E6575E/16 zu SU 845080 A.

* cited by examiner

Primary Examiner—Helen Kwok
(74) Attorney, Agent, or Firm—Bacon & Thomas, PLLC

(57) ABSTRACT

A method is described for testing thin material wherein the material is irradiated with ultrasonic waves at least in certain areas and transmission of the ultrasonic waves through the material is determined and evaluated. The transmission of ultrasonic waves of different frequencies is thereby determined. The differences of the transmission at the different frequencies are then used to determine a criterion for evaluating the quality, in particular the porosity, of the irradiated material. Furthermore, a corresponding test device is described.

23 Claims, 2 Drawing Sheets

0
METHOD AND APPARATUS FOR TESTING THIN MATERIAL

BACKGROUND OF THE INVENTION

This invention relates to a method for testing thin material, for example paper, foils or other sheet material, wherein the material is irradiated with ultrasonic waves at least in certain areas and transmission of the ultrasonic waves through the material is determined and evaluated. In addition, the invention relates to a corresponding test device.

Such methods and test devices are used to determine the weight per unit area or thickness of the material in noncontacting fashion by ultrasonic transmission, whereby the ultrasonic transmission is generally in inverse proportion to the local weight per unit area. An example of such a method is described in DE 30 48 710 C2. A typical field of application is the testing of bank notes in automatic tellers or bank note sorters. The bank notes are guided between ultrasonic transmitters and ultrasonic receivers so that the bank note is tested at least along a given track.

Ultrasonic transmission measurements can be used to discover not only the thickness or weight per unit area of the material but also tears or holes in the material. This is described for example in U.S. Pat. No. 4,519,249, where a roller system is used to curve the bank notes during ultrasonic irradiation far enough for the tears or holes to open sufficiently. The ultrasonic waves then pass through the tear or hole unhindered. In perfect bank notes the transmission value is only about 1%, while at holes or tears in the bank notes the transmission is 100%. Such places therefore yield clear peaks in the measuring pattern.

In the course of investigations done by the applicant in connection with the present invention, it has proved disadvantageous in these known methods that they are e.g. unable to recognize porous areas in the material that consist of pores invisible to the naked eye and that this may falsify the determination of the weight per unit area. This problem occurs in particular with specimens such as bank notes that have been in circulation for some time. In this case, frequent bending of the material may have produced porous areas at certain places in the course of time. These porous places show an increased transmission value compared to the transmission value of the undamaged material. According to the applicant's investigations, the problem of recognizing such places in a test consists in that an increased transmission value is not necessarily due to porosity in the case of a struc-structured material such as a bank note. A bank note may thus have e.g. intentionally thinner places or places of different density at certain places, for example in the area of a watermark or another security feature, or microperforations as a further security feature. An increased transmission value can therefore also be due to desired structures or features in a perfect bank note. If a transmission value of about 1% is assumed for a perfect bank note for example, a porous place would have a transmission value of 3 to 4% for example. However, a perfect bank note could likewise have a transmission value of 3 to 4% at a certain, intentionally thinner place, said value not being distinguishable from the transmission value of a porous place.

SUMMARY OF THE INVENTION

It is the problem of the present invention to provide an alternative that makes it possible to detect defective, in particular porous, places very clearly in a simple way during testing and to distinguish them from intentionally thinner places in the material for example.

This problem is solved by a method and a test device according to the independent claims. The dependent claims relate to especially advantageous embodiments and developments of the inventive method and test device.

The inventive solution is likewise based on transmission measurement of ultrasonic waves. The essential point is that the transmission of ultrasonic waves is determined at different ultrasonic frequencies. Measurement is done at least at two different frequencies. The differences of the transmission at the different frequencies are used to determine a certain criterion, such as the difference of the transmission values or a quotient of the transmission values, for evaluating the quality of the material under test.

This idea is based on the finding that, for normal, undamaged paper, the transmission is in inverse proportion not only to the weight per unit area but also to the frequency. In a defective, porous area the deviation from this law is the greater the higher the ultrasonic frequency is, due to the frequency dependence of the diffraction on the pores. This means that the positive deviation of the measured transmission in the area of a porous place from the transmission value of undamaged material is higher for example for short-wave ultrasonic waves than for long-wave ultrasonic waves. The differences in the intensity meas-measured in transmission at the different frequencies can consequently be used to obtain information in a simple way about the presence of places of increased porosity.

A corresponding test device includes not only an ultrasonic transmitting device for irradiating the material under test from one side at least in certain areas and an ultrasonic receiving device for measuring the intensity of the ultrasonic waves transmitted through the material on the other side of the material, but also a suitable evaluation device for evaluating the determined transmission of the ultrasonic waves. The ultrasonic transmitting device and/or the ultrasonic receiving device are designed such that the transmission of ultrasonic waves can be determined at different frequencies. The evaluation device must accordingly be able to determine a criterion for evaluating the quality of the irradiated material by the differences of the transmission at the different frequencies.

In one embodiment, the material is irradiated with ultrasonic waves at exactly adjusted discrete, i.e. single, different frequencies, for example exactly two different frequencies. The term "discrete frequencies" is to be understood here to include narrow-band frequency ranges around the particular desired frequency.

Irradiation at discrete different frequencies is to be realized for example by having the ultrasonic transmitting device include different transmitters each emitting ultrasonic waves of a certain frequency or narrow-band frequency range. However, the ultrasonic transmitting device used can also emit ultrasonic waves of an exactly defined spectrum, for example at two discrete different frequencies simultaneously.

If the transmitting device emits at exactly defined, discrete frequencies, the ultrasonic receiving device may be constructed so as to detect only frequencies in these ranges, i.e. it can for example likewise consist of individual receivers each measuring selectively only one frequency. However, the receiving device may also be one that detects ultrasonic waves of a great variety of frequencies in a broad band and thus records a broad transmission spectrum. In this case, however, it must be ensured that the ultrasonic waves of the different frequencies can be separated from each other. This may be done for example by means of software when a frequency spectrum is recorded by the receiving device in that device in that only the measured values at the certain frequencies are taken into account during evaluation.

Another way of guaranteeing separation of the different frequencies is not to emit at the different frequencies simultaneously but one after the other, it being taken into account during measurement or evaluation at what time ultrasound was emitted at what frequency.

In an alternative embodiment, the ultrasonic transmitting device irradiates the material with ultrasonic waves with a continuous broad frequency spectrum. This is followed for example by selective measurement on the receiver side, i.e. either only certain frequencies are registered by the receiver or only the measured values at certain frequencies are taken into account in a following step.

One way of emitting ultrasonic waves with a broad frequency spectrum is to have the ultrasonic transmitting device irradiate the material with short ultrasonic wave pulses. As is well known, the frequency spectrum of a pulse is the broader the shorter a pulse is. Preferably, the pulse length is less than a few microseconds.

According to the preferred embodiment, the criterion for porosity is a quotient formed of the determined transmission values from ultrasonic waves of two different frequencies. Since the transmission in a perfect material is in inverse proportion to the frequency and to the weight per unit area of the material, the quotient of the intensities measured in transmission of the ultrasonic waves of the two different frequencies is always constant in a perfect specimen. It only deviates from this constant value at porous places, so that these places can be discovered in a simple way.

In cases where ultrasonic waves with a broad-band frequency spectrum are used—for example by emission of short ultrasonic wave pulses—and the total transmission spectrum is measured and recorded, it is also possible to obtain a criterion for quality evaluation by registering a change of the transmission spectrum in dependence on the irradiated place. One way of realizing this is to permanently record the measured transmission spectrum of the ultrasonic waves and compare it with prior measurements.

Since the pulse shape is further likewise determined by the spectrum of the frequency components contained in the pulse, it is preferably also possible to find the porous places directly by analysis thereof.

In an inventive test, the number of porous places in a certain piece of material (specimen) can be determined for example. An extension of porous places within a specimen can likewise be detected.

In an especially preferred example, a limiting criterion is defined, for example a maximum number of porous places and/or a maximum extension of porous places. If this limiting criterion is exceeded in a specimen, the specimen is rejected as defective; the relevant bank note is shredded for example in the case of bank notes.

The ultrasonic waves used are preferably in a frequency range of 50 to 400 kilohertz. In order to achieve a clear effect during testing and be able to recognize porous places sufficiently clearly, the frequencies or frequency ranges in question should be sufficiently far apart. When using ultrasonic waves of two different frequencies, the greater of the two frequencies is preferably about 1.5 to 3 times the smaller frequency.

BRIEF DESCRIPTION OF THE DRAWINGS

The invention will be explained in more detail in the following by an example with reference to the enclosed figures, in which.

DETAILED DESCRIPTION OF THE INVENTION

Figure 1:
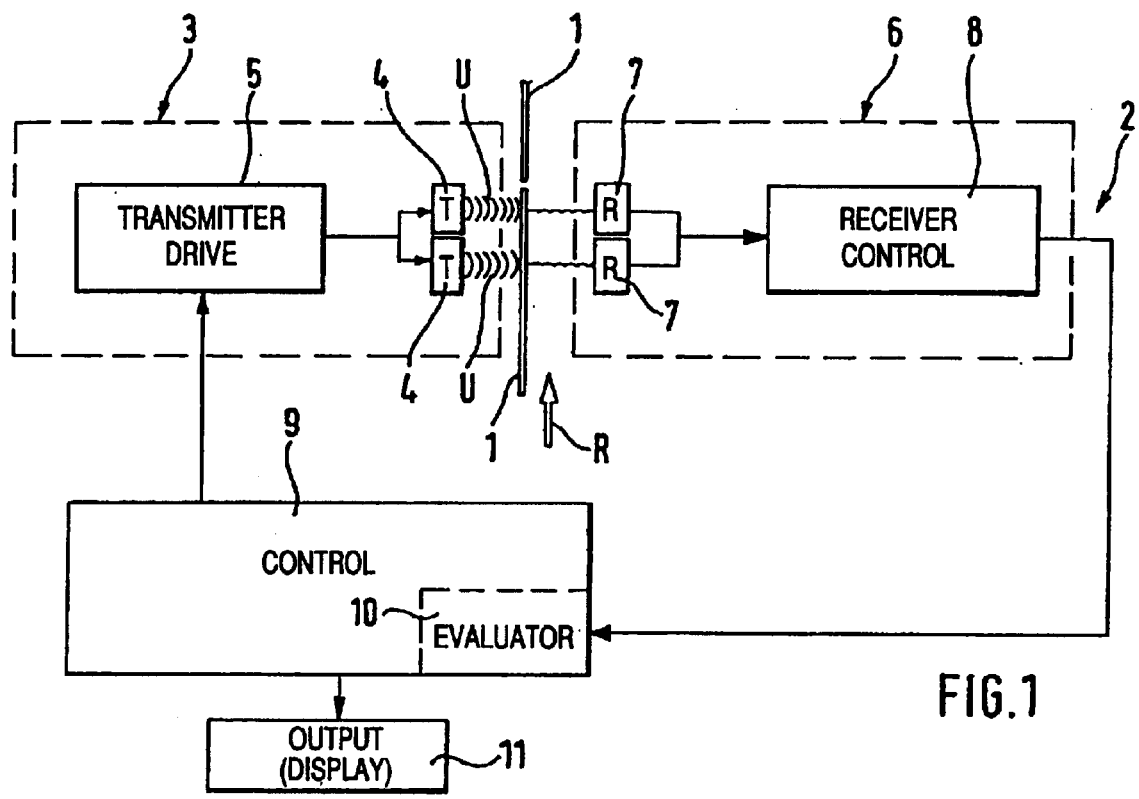
FIG. 1 shows a schematic block diagram of an inventive test device.

FIG. 1 shows an example of inventive test device 2 for testing bank notes 1. Such a test device 2 is located for example within a bank note sorter (not shown).

Test device 2 has, firstly, ultrasonic transmitting device 3 and, secondly, ultrasonic receiving device 6. Ultrasonic transmitting device 3 consists here of a plurality of transmitters 4 and transmitting drive 5 for driving individual transmitters 4. Likewise, ultrasonic receiving device 6 consists of one or more receivers 7 each connected with receiver control 8 which reads out the measured values present on receivers 7.

Transmitting drive 5 is controlled by controller 9 of test device 2. Part of controller 9 is evaluation device 10 which accepts the data from receiver control 8 and evaluates them. Controller 9 can be for example a computer or microcontroller, evaluation device 10 being realized in the form of suitable software. Departing from the shown example, transmitting drive 5 and receiver control 8 can likewise be integrated in said controller 9, also by means of software.

Further, controller 9 has connected thereto output device 11, for example a display, that for example informs an operator of test device 2 when a defective bank note 1 runs through test device 2. Output device 11 may also be an interface that connects inventive test device 2 with a superordinate controller of the bank note sorter and thus e.g. automatically induces rejection of defective bank note 1.

Transmitters 4 of transmitting device 3 and receivers 7 of ultrasonic receiving device 6 are disposed accordingly opposite each other. Bank notes 1 under test are drawn between transmitters 4 and receivers 7 in draw-through direction R and thereby irradiated with ultrasonic waves U on one side by transmitters 4. Receivers 7 then measure the intensity of the transmitted component of ultrasonic waves U on the other side.

Figure 2:
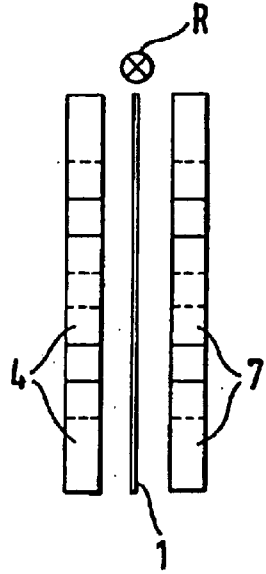
FIG. 2 shows a schematic side view of an arrangement of ultrasonic transmitters and ultrasonic receivers viewed in the draw-through direction of a specimen.
Figure 3:
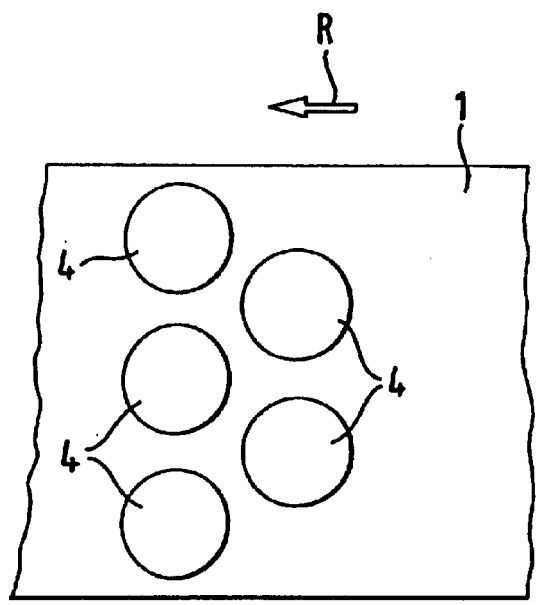
FIG. 3 shows a schematic representation of the spatial arrangement of the transmitters of FIG. 2 in a plan view.

FIGS. 2 and 3 show the exact arrangement of individual transmitters 4 and receivers 7 disposed accordingly on the other side of bank note 1 under test. As indicated by these figures, a plurality of transmitters 4 are disposed in a first row perpendicular to draw-through direction R distributed over the total width of bank note 1. Each of said transmitters 4 irradiates an exactly defined track along draw-through direction R on traversing bank note 1. Further transmitters 4 are located offset in parallel in front of or behind said first row of transmitters 4 for exactly covering the gaps between transmitters 4 of said first row. This guarantees that bank note 1 is tested over its total area.

As is apparent from FIG. 2, receivers 7 are disposed opposite transmitters 4 in exactly the same way.

In the present example, the transmitters each emit at exactly two defined frequencies $f_1$ and $f_2$, higher frequency $f_1$ having about 1.5 to 3 times the value of lower frequency $f_2$. Receiving device 6 is able to measure the ultrasonic waves separately for said two frequencies $f_1$ and $f_2$ or in the respective frequency ranges.

Figure 4:
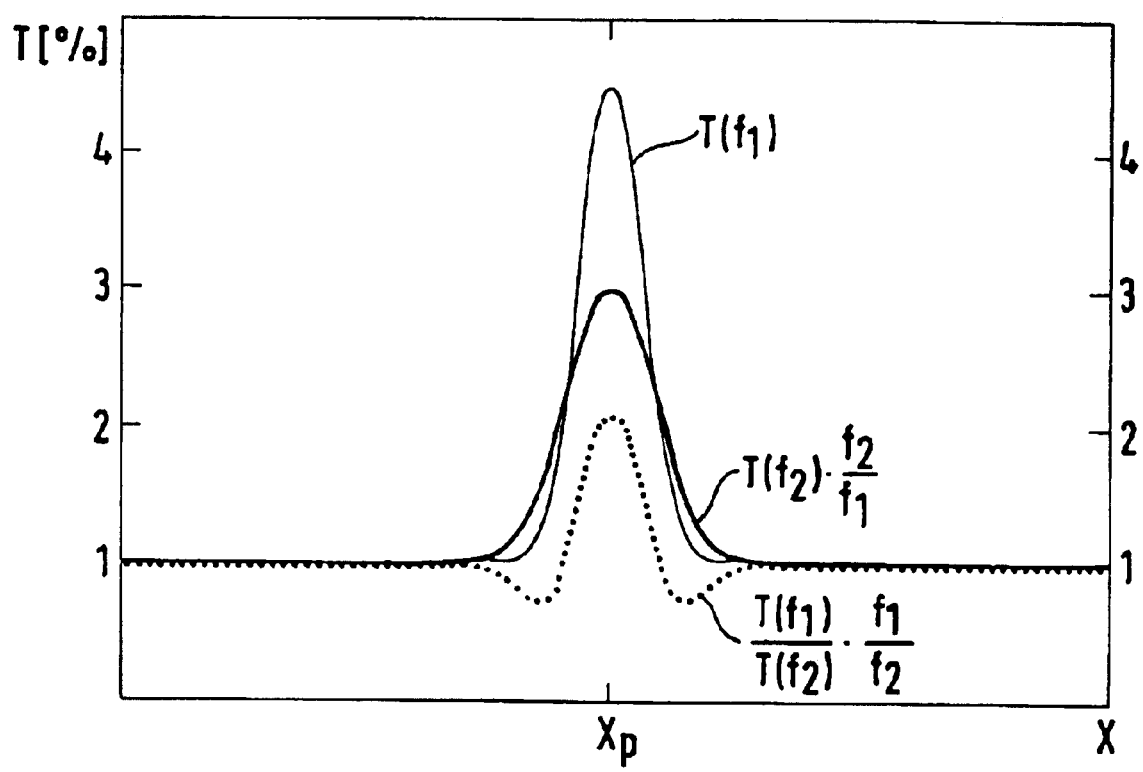
FIG. 4 shows a diagram of the intensity for two different frequencies and the function of the quotient from the two intensity measurements over the measuring point.

A typical measuring curve is shown in FIG. 4. This diagram records particular transmission value T ($f_1$), ($f_2$)× $f_2/f_1$ normalized for frequency $f_1$, i.e. the intensity measured in transmission based on the total emitted intensity, for desired frequencies $f_1$ and $f_2$ over irradiated place x, i.e. along a track on bank note 1. The third, dotted curve shows the quotient from these two measuring curves T ($f_1$)×$f_1$ and T ($f_2$)×$f_2$. Normalized transmission values T ($f_1$), T ($f_2$)×$f_2/f_1$ are constant over quite a distance in this example (being 1% for example), then rise suddenly at certain place $x_p$ and subside to the normal value. Said place $x_p$ is a place of increased transmission.

If place $x_p$ simply had a lower weight per unit area, being for example a thinner place on bank note 1, this reaction would be frequency-independent and the relative increase of transmission values T ($f_1$), T ($f_2$)×$f_2/f_1$ would be equal at both frequencies $f_1$, $f_2$. The dotted curve produced from the quotient of the transmission values would then remain constant, the individual measuring curves showing a peak of equal height.

In the shown example, however, the place on bank note 1 is porous, i.e. defective. At said place $x_p$ measured transmission value T ($f_1$) is relatively higher at the maximum for greater frequency $f_1$ than for the ultrasonic waves of lower frequency $f_2$ due to the frequency dependence of the diffraction on the pores. In the shown example, measured transmission value T ($f_1$) increases by a factor of 3 at porous place $x_p$ for greater frequency $f_1$, and only by a factor of 2 for the ultrasonic waves of smaller frequency $f_2$. Consequently, the curve formed from the quotient of transmission values T ($f_1$), T ($f_2$)×$f_2/f_1$ also has a clear peak at said place $x_p$. Thus the porous place can be clearly identified in a simple way. The different width of the peaks is likewise due to the frequency dependence of the diffraction.

If place $x_p$ was not a porous place but an intact place with half the weight per unit area relative to the surrounding area, the transmission curves in FIG. 4 would likewise have a maximum for frequencies $f_1$ and $f_2$. However, the associated quotient curve would in this case largely show a straight course, i.e. at place $x_p$ it would have a value corresponding substantially to the quotient value at the adjacent places with higher weight per unit area.

In the aforementioned example, the inventive method has been described in connection with the testing of bank notes 1 as an example of a document of value, since the problems of known methods that are solved by the invention arise in particular with such materials that are usually not of completely homogeneous form.

However, the invention can be used with equal success for other test objects, for example paper webs, foil webs or similar thin material.

What is claimed is:

1. A method for contactlessly testing banknotes wherein a banknote is irradiated with ultrasonic waves at least in certain areas and transmission of the ultrasonic waves through the banknote is determined and evaluated, comprising determining the transmission of ultrasonic waves at different frequencies and establishing at least one criterion for evaluating the quality of the irradiated banknote according to the differences of transmission at the different frequencies, wherein said at least one criterion is dependent on the frequency dependence of the diffraction on pores of the banknote.

2. The method according to claim 1, wherein the criterion enables evaluating the porosity of the banknote.

3. The method according to claim 2, wherein a number of porous places and an extension of porous places of a piece of a banknote under test is determined and the piece of the banknote is rejected as defective above a maximum number or a maximum extension of porous places defined as a limiting criterion.

4. The method according to claim 1, wherein the banknote is irradiated with ultrasonic waves at discrete different frequencies.

5. The method according to claim 4, wherein the banknote is irradiated by different transmitters each emitting ultrasonic waves of a certain frequency.

6. The method according to claim 1, wherein the banknote is irradiated with broad-band ultrasonic waves having a broad frequency spectrum.

7. The method according to claim 6, wherein a transmission of broad-band ultrasonic waves is determined for a plurality of discrete frequencies and used for evaluation.

8. The method according to claim 6, wherein a change of a measured broader transmission spectrum of broad-band ultrasonic waves is determined and is used to establish a criterion for quality evaluation.

9. The method according to claim 1, including using short ultrasonic wave pulses for irradiating the banknote.

10. The method according to claim 9, wherein the criterion for quality evaluation is determined from a comparison of the pulse shape of the ultrasonic wave pulses before and after transmission through the banknote.

11. The method according to claim 1, wherein the criterion for quality evaluation is a quotient formed of determined transmission values of ultrasonic waves of two different frequencies.

12. The method according to claim 11, wherein, one of the frequencies is roughly 1.5 to 3 times the other frequency.

13. A test device for contactlessly testing banknotes, comprising an ultrasonic transmitting device arranged to irradiate a banknote under test with ultrasonic waves from one side at least in certain areas thereof, an ultrasonic receiving device arranged to measure the intensity of the ultrasonic waves transmitted through the banknote on the other side of the banknote, and an evaluation device configured to evaluate the determined transmission of the transmitted ultrasonic waves, wherein the ultrasonic transmitting device and/or the ultrasonic receiving device are configured to operate at different ultrasonic wave frequencies during testing of the banknote, the evaluation device is configured to establish a criterion for evaluating the quality of the irradiated banknote according to the differences of the transmission at the different frequencies, and wherein said at least one criterion is dependent on the frequency dependence of the diffraction on pores of the banknote.

14. The test device according to claim 13, wherein the ultrasonic transmitting device is arranged to irradiate the banknote with ultrasonic waves at discrete different frequencies.

15. The test device according to claim 14, wherein the ultrasonic transmitting device includes different ultrasonic transmitters each emitting ultrasonic waves of a certain frequency.

16. The test device according to claim 13, wherein the ultrasonic transmitting device is arranged to irradiate the banknote for testing with broad-band ultrasonic waves having a broad frequency spectrum.

17. The test device according to claim 16, wherein the ultrasonic receiving device is arranged to determine transmission of broad-band ultrasonic waves for a plurality of different discrete frequencies.

18. The test device according to claim 17, wherein the evaluation device is arranged to use values of a measured transmission spectrum of the broad-band ultrasonic waves at a plurality of discrete frequencies for evaluation.

19. The test device according to claim 16, wherein the evaluation device includes a transmission spectrum change determining arrangement configured to determine a change in a transmission spectrum of the broad-band ultrasonic waves.

20. The test device according to claim 13, wherein the ultrasonic transmitting device is configured to irradiate the banknote under test with short ultrasonic wave pulses.

21. The test device according to claim 20, wherein the evaluation device includes a pulse shape change determining arrangement configured to determine a change of the pulse shape of the ultrasonic wave pulses before and after transmission through the banknote.

22. The test device according to claim 13, wherein the ultrasonic receiving device includes different ultrasonic receivers each responsive to ultrasonic waves of a certain frequency.

23. The test device according to claim 13, wherein the evaluation device includes a quotient calculating device arranged to determine a quotient of determined transmission values of ultrasonic waves of two different frequencies.

* * * * *